(12) United States Patent
Wilkinson

(10) Patent No.: US 7,845,942 B2
(45) Date of Patent: Dec. 7, 2010

(54) TOOTH PREPARATION INSTRUMENT AND SYSTEM OF ITS USE

(76) Inventor: Alfred Harper Ben Wilkinson, 373 Spring St., Spencer, TN (US) 38585

( * ) Notice: Subject to any disclaimer, the term of this patent is extended or adjusted under 35 U.S.C. 154(b) by 210 days.

(21) Appl. No.: 12/155,423

(22) Filed: Jun. 4, 2008

(65) Prior Publication Data

US 2008/0318187 A1    Dec. 25, 2008

Related U.S. Application Data

(60) Division of application No. 10/921,827, filed on Aug. 20, 2004, now Pat. No. 7,393,211, which is a continuation-in-part of application No. 10/329,832, filed on Dec. 27, 2002, now Pat. No. 7,004,757, which is a continuation-in-part of application No. 09/976,214, filed on Oct. 15, 2001, now Pat. No. 6,511,323.

(51) Int. Cl.
*A61C 19/04* (2006.01)
*A61C 9/00* (2006.01)

(52) U.S. Cl. ............... 433/72; 433/70; 433/71; 433/214; 433/37; 433/44

(58) Field of Classification Search ............ 433/72
See application file for complete search history.

(56) References Cited

U.S. PATENT DOCUMENTS

| | | | |
|---|---|---|---|
| 1,323,832 A * | 12/1919 | Chige | 433/46 |
| 1,367,628 A * | 2/1921 | Roach | 433/46 |
| 2,598,927 A * | 6/1952 | May | 433/47 |
| 2,758,374 A * | 8/1956 | Fisher et al. | 433/37 |
| 3,445,935 A | 5/1969 | Marshall | |
| 3,508,334 A | 4/1970 | Weissman | |
| 3,838,517 A | 10/1974 | Michnick | |
| 3,979,829 A | 9/1976 | Lemos | |
| 4,144,645 A | 3/1979 | Marshall | |
| 4,353,696 A | 10/1982 | Bridges | |
| 4,473,354 A | 9/1984 | Rigaud | |
| 4,526,542 A | 7/1985 | Kochis | |
| 4,941,826 A | 7/1990 | Loran et al. | |
| 5,545,039 A | 8/1996 | Mushabac | |
| 5,575,656 A | 11/1996 | Hajjar | |
| 5,580,244 A * | 12/1996 | White | 433/37 |
| 5,941,706 A | 8/1999 | Ura | |
| 6,298,587 B1 * | 10/2001 | Vollom | 40/427 |

(Continued)

*Primary Examiner*—Cris L Rodriguez
*Assistant Examiner*—Yogesh Patel
(74) *Attorney, Agent, or Firm*—Jacobson Holman PLLC

(57) ABSTRACT

A dental impression analyzer including a housing having two opposite open ends. A lower end of the two opposite ends fits over a tooth of a patient. A plurality of pins are slidably mounted in the housing. The pins are of equal length, extending parallel to each other, and at least a portion of sidewalls of the housing extending parallel to each other and parallel to the plurality of pins to maintain the pins parallel to each other and to guide movement of the pins. The plurality of pins are tightly compressed together in an interior of the housing. A lower end of the pins are positioned to engage an uppermost surface of the tooth of the patient when the housing is fitted over the tooth of the patient. An upper end of the pins replicates the uppermost surface of the tooth when the lower end of the pins engage the uppermost surface of the tooth.

6 Claims, 13 Drawing Sheets

U.S. PATENT DOCUMENTS

| | | | |
|---|---|---|---|
| 6,379,147 B1 * | 4/2002 | Georgakis et al. | 433/37 |
| 6,511,323 B1 | 1/2003 | Wilkinson | |
| 6,633,416 B1 * | 10/2003 | Benson | 358/478 |
| 6,913,461 B2 * | 7/2005 | Gittleman | 433/38 |
| 6,925,205 B2 | 8/2005 | Leedham et al. | 382/167 |
| 6,964,567 B2 | 11/2005 | Kerschbaumer et al. | 433/26 |
| 2003/0207235 A1 | 11/2003 | Van der Zel | 433/223 |

* cited by examiner

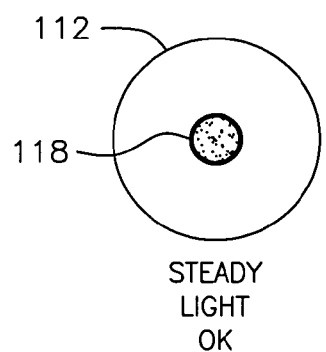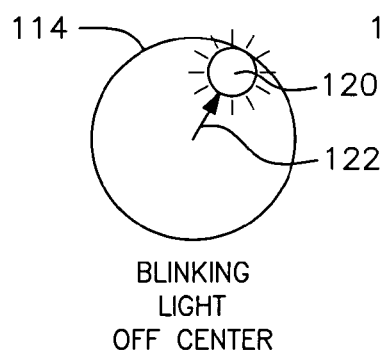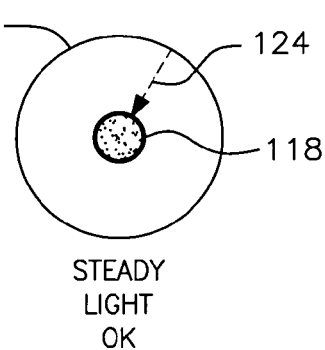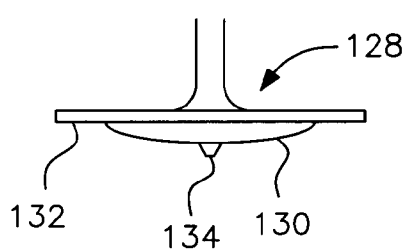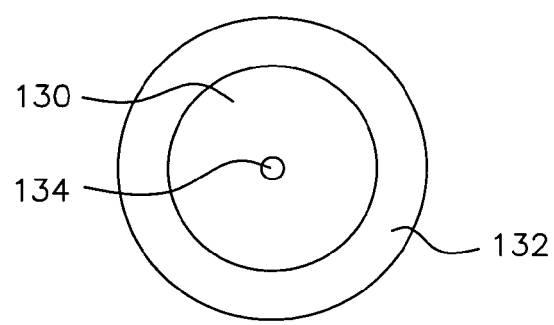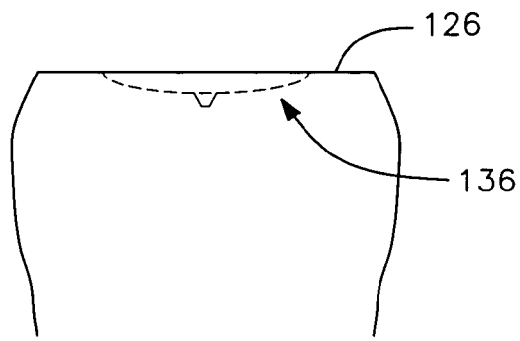

TOOTH PREPARATION INSTRUMENT AND SYSTEM OF ITS USE

This application is a Divisional of application Ser. No. 10/921,827 filed Aug. 20, 2004 now U.S. Pat. No. 7,393,211, which is a continuation-in-part application of Ser. No. 10/329,832, filed Dec. 27, 2002, now U.S. Pat. No. 7,004,757, which is a continuation-in-part application of Ser. No. 09/976,214, filed Oct. 15, 2001, now U.S. Pat. No. 6,511,323 and hereby incorporated in their entirety by reference.

FIELD OF THE INVENTION

The present invention consists of a tooth preparation instrument and system that creates a tapered conical shape from a tooth, with pre-determined dimensions, making it possible for a lab technician to independently and simultaneously create a crown that exactly fits the prepared tooth. The crown is ready for permanent placement on the prepared tooth at the time of preparing the tooth. Use of the invention saves considerable time and effort as compared with current methods.

BACKGROUND OF THE INVENTION

Currently, a tooth is prepared for a crown in the following manner. First, during an initial office visit, the dentist makes an impression of the portion of the mouth in which the tooth is located, with upper and lower occlusal surfaces. From this impression a lab technician will later create a stone study model.

The dentist then removes tooth material with a high-speed drill, relying on eyesight and expertise to create a form on which a crown will be cemented. This form begins with a narrow shoulder at the gum line and tapers inward as it rises to a flattened top that ends just below the lowest level of the tooth's original biting surface.

The dentist then makes an impression of the prepared tooth and sends it to the lab technician along with the original tooth impression, prepared prior to removal of tooth material. The dentist makes and installs a temporary crown for the prepared tooth.

Using the impression of the prepared tooth, the lab technician produces a crown that matches the dentist's color and material specifications and sends it to the dentist. At the patient's second visit, the dentist tests and adjusts the crown as necessary before cementing it in place.

SUMMARY OF THE INVENTION

By the present invention, the following steps will be performed. At an initial office visit, the dentist makes an impression of the portion of the mouth in which the tooth is located, with upper and lower occlusal surfaces. From this impression the lab technician will later create a stone study model.

The dentist, at a second office visit or, in a preferred embodiment, during the same office visit when a lab technician is available in the office for simultaneous creation of the crown, presses a surface contour tool against the biting surface of the tooth to determine the depth settings for at least one burr in a surface tool that will remove the upper surface of the tooth and create a working surface for the material removal device.

The dentist inserts at least one burr with the proper length in this tool so that when the tool is lowered onto the tooth, a flat surface will be created. It is essential that this surface be aligned perpendicular to the center line of the tooth. The dentist also calculates the center of the tooth and sets the depth of the burr that will drill the center hole for guiding the material removal device.

The flat surface tool and the center hole drilling burr are operated with a device that locks onto the tooth and ensures that the top surface of the prepared tooth will be perpendicular to the central line of the tooth. The dentist makes two calculations. First, the distance is calculated in 0.1 mm increments between a predetermined point below the lowest level on the tooth's biting surface (beginning level) and the gum line (ending level). This will be the height of the prepared tooth. The second calculation is the distance from the center of the tooth's biting surface to a predetermined point inside the narrowest part of the tooth at the gum line (the shoulder). This will be the radius at the shoulder of the prepared tooth. The dentist inserts tapered burrs of predetermined lengths and a guide pin of the required length into the material removal device and feeds the calculations into a computer processor which will control the material removal device. A print out of the calculations is forwarded to the technician for confirmation of the requirements for the prepared crown or a bridge.

To initiate operation of the material removal device, a center hole is drilled. A flat surface tool is used to remove tooth material, smoothing the surface as necessary. The dentist inserts the guide pin of the material removal device in the center hole and begins to remove material from the side of the tooth. Each cycle around the tooth removes 0.1-0.5 mm. The various burrs are tapered and may be diamond burrs to create the required chamfer on the sides of the tooth.

The device has four computer controlled lights to guide the dentist. A green light indicates that the device is level with the top surface. A blue light is activated when a desired depth is achieved as also limited by the length of the burr. Two lights (one red and one yellow) warn the dentist that the device is tilted so that it is creating an undercut (red) or drilling too far toward the outer edge of the shoulder (yellow).

After each cycle, the dentist moves the depth setting another 0.1-0.5 mm until the required depth is reached. The burrs on the device, ranging in number from one to six, are preset so that they cannot be extended beyond the depth that has been calculated by the dentist.

While the dentist has been removing tooth material the lab technician has finished the crowns, bridges, veneers, implants or either porcelain or composites independently and simultaneously, if the technician is immediately available, produced a crown or bridge that will fit the prepared tooth. The prepared crown will have the same internal dimensions as the prepared tooth and also the same characteristics (color, shape) as the original tooth. Preformed porcelain veneers and implant crowns are very important, save a lot of time and may be added like other preformed crowns.

Some of the advantages of the invention are that a dentist can prepare a tooth knowing that the crown will fit precisely, because the prepared tooth will have the same exterior dimensions as the interior opening on the crown so that the crown will precisely fit the prepared tooth. In addition, only one office visit is necessary to prepare the tooth and install a permanent crown. A patient will not require a temporary crown. The dentist will not have to make an impression of the prepared tooth and wait for the technician to produce the crown.

Alternatively, a series of pre-prepared crowns of various shapes and colors may be available to the dentist. Since the tooth will be prepared to a predetermined truncated cone size, pre-formed crowns having a similar pre-formed internal truncated conical recess may be available to the dentist. This would insure immediate accurate crown installation during a single office visit.

In an alternate form of the present invention, it is known that the occlusal surface of a tooth varies in depth, in that it is not perfectly flat, and in its perimeter outline, it is not perfectly circular. The purpose of the present invention is to make it much easier for a dentist to prepare a tooth for a crown in a way that will accomplish the following objectives:

prepare a predictable and symmetrically consistent conical shape for the tooth that is truncated horizontally at the occlusal surface, at a level that is at least 1 mm below the lowest point on the tooth's original occlusal surface, and tapers slightly (i.e. 5 to 7 degrees) outward toward the gum-line and terminates in a shoulder at the gum-line that is about 1.5 mm wide; and ensures that the technician has the exact dimensions and shape of the prepared tooth so that the technician can quickly prepare a crown that fits.

The present invention consists of the following steps:

The dentist uses a probe to determine the dimensions and shape of the tooth and stores those dimensions in a computer, which transmits the data to the technician's computer. The technician can also prepare the die of the study model assuming that data is transmitted to the dentist's computer. The dentist then prepares a study model of the tooth and sends it to the technician. In this and all subsequent steps it may be assumed that data is transmitted from the dentist's computer to that of the technician.

Using an intra-oral digital camera, the dentist makes a hue, chroma, and value analysis of the labial surface of the patient's nearby central, lateral and cuspid teeth and scans this information into the computer. Using this analysis and information received directly from the dentist about other characteristics of the patient's teeth such as translucency, the technician is able to determine coloring for the crown that will match the patient's existing teeth.

Prior to beginning preparation of the tooth, the dentist removes any fillings or decay and repairs any areas of structural weakness and then replaces the removed material(s) with a composite or other material that will replicate the hardness and strength of the original tooth, keeping the shape of the tooth as close as possible to its original shape.

The dentist uses a large diameter burr to remove the highest spots on the occlusal surface of the tooth, but not below the lowest level on the original surface.

Using a flat disk-burr, the dentist removes dental material to a point where the highest part of the prepared tooth will be 1 mm below the lowest point on the original occlusal surface, maintaining the shaft of the burr along the central longitudinal axis of the tooth. During the removal process in this step, the dentist's computer monitors the orientation of the hand-piece so that the shaft of the disk burr is kept parallel to the central, longitudinal axis of the tooth. The tooth removal device is equipped with a display monitor that shows a steady green light in the center of a circle to indicate to the dentist when the shaft is correctly oriented; any deviation causes this light to move off center and blink until the deviation is corrected and the light is back in the center of the circle. Blinking of the light speeds up if deviation increases, so the dentist can quickly make the necessary correction. As a result, the final occlusal surface on the prepared tooth will be perpendicular to the central longitudinal axis of the tooth, with a small positioning hole in its center.

The dentist determines the final diameter of the occlusal surface, and inputs that dimension in the computer. The dentist then selects a disk-burr with a slightly smaller diameter than the flattened occlusal surface and that has a slight convex bottom. Using the burr, the dentist excavates a slight central depression that rises upward to the flat portion of the occlusal surface. In the center of the depression, the disk-burr drills a small positioning hole.

For each convex bottom disk-burr there is a matching disk-post that fits the depression created by the disk-burr. Each disk-post has a protrusion extending from the center of its bottom surface and a post extending from a center of its top surface so that when the disk-post is in position it will be aligned with the central longitudinal axis of the tooth. The dentist applies a bonding agent to the outer bottom edges of the disk-post and positions the disk-post in the depression created by the disk-burr, with the disk-post's protrusion seated in the positioning hole created by the disk-burr.

For each disk-post there is a matching set of radial arms, each arm having a different angle (e.g. 5, 6 or 7 degrees) at the distal end of the arm.

Removal burrs used with the radial arms have two abrasive surfaces: one on the distal terminal end, which is slightly convex, and the other around its entire circumference. The working diameter of the removal burr depends on the width of the shoulder desired as well as the distance between the center of the tooth and the point on the perimeter of the tooth at the gum line that is nearest the center. The objective is to create a shoulder that at a minimum is 1.3-1.5 mm wide at the nearest point. The dentist places the radial arm on the disk-post, fixes the hand-piece to the radial arm, inserts the removal burr with the selected diameter, and begins removing dental material from the side of the tooth.

As soon as the burr has completed a circuit of the tooth, the distance covered is recorded and the dentist extends the burr an additional 1 mm for the next circuit. The dentist stops removal when the removal burr has reached the higher shoulder level (Y-$1a$). The distance from the occlusal surface down to the shoulder level (Y-$1a$) is recorded.

Beginning on the labial side of the tooth, the dentist removes additional dental material in the area of the lower shoulder. The first pass over this lower area will establish the limits for the area, and from that point a computer will restrict further removal to the area between those limits. The dentist continues removing material down to the lower shoulder level. When the dentist stops, the additional distance covered by the burr (between levels Y-1 and Y-$1a$) is recorded.

Moving around the tooth, the burr not only removes just enough material to create an angled (depending on the angle of the moving end of the radial arm) straight line down to both shoulder levels at the gum-line, creating two shoulders that are at least 1-1.5 mm wide. The width of the shoulder depends on the diameter of the burr, which is determined by the dentist by calculating the difference between the point on the gum-line circumference that is farthest from the center and the one that is closest to the center. That difference, plus 1.5 mm, will create a shoulder that is at least 1.5 mm wide and reaches the edge farthest from the center. An additional advantage presented by the convex-bottomed burr is that it will create a shoulder that slopes downward toward the center of the tooth.

The dentist repeats the previous step on the lingual (buccal) side of the tooth.

The dentist uses an intra-oral digital camera to survey the bottom perimeter of the prepared tooth in relation to the outside edge of the tooth at the gum-line. Using the data received, the computer generates an outline image of the shoulder at the gum-line that shows width variations.

The dentist makes a final check with the technician to confirm that both computers are dealing with identical final dimensions for the prepared tooth. The technician can also finish the work two or three weeks prior to preparation.

Some advantages of the present invention include the disk-post providing a support for the radial arm that circuits the tooth being more stable than a projection going down into dental material.

The required angle on the prepared tooth is obtained by having the radial arm hold a straight burr removing material at a predetermined angle which is preferable to using a chamfered burr. A chamfered burr may not cut a consistent surface going down to two different levels (and might also make contact with a neighboring tooth).

By using a removal burr that has a convex abrasive surface at its end, shoulders are created that are not only slightly concave but also slope slightly upward toward their outer edge, making for a more secure fit of a crown.

By using a convex bottom on the disk-burr, when leveling off the occlusal surface, the dentist avoids having to do a separate operation later in order to remove dental material on the occlusal surface so that the anatomy of the crown can be easily accommodated.

Another aspect of the present invention includes a dental computer analyzer designed to analyze a crown preparation and measure, in microns, a digital image (still or video) of the prepared tooth as compared to a pre-prepared model. The results are displayed on a television monitor. This system may be used on porcelain veneers, porcelain crowns, bridges and implants.

The difference between a prepared tooth and a model of the intended crown are used by the dentist to ensure a proper fit. The dentist puts the dental computer analyzer in the mouth of the patient to visually indicate a difference between the prepared crown and a model of a die used to prepare the crown. The proposed crown may be present with the dentist or, alternatively, an electronic image may be conveyed to the dentist based upon a prepared tooth retained by a dental technician.

Both the prepared tooth and the pre-prepared model of an appropriate die to form a proper fitting crown are initially displayed in a side by side comparison on a television monitor. The two samples (the prepared tooth and the pre-prepared die for forming a crown) are, by computer software, rotated for visual signs of discrepancies between their images. Then the two similarly oriented images are superimposed on one another to ensure an identical fit as the two superposed images are also simultaneously rotated while maintaining their relative orientation.

Computer markings can be imposed to coordinate a location of the prepared tooth compared to the die. Corrections on the prepared tooth may thereby be easily facilitated by knowing where changes in the prepared tooth need to be made. The computer images can be sent electronically to a technician for altering a prepared crown.

A further aspect of the present invention includes a computer impression analyzer. A series of metal or plastic pins are arranged in a pin holder which is fit over a prepared tooth. The pins are slidably mounted in the holder so that upon contacting the prepared tooth, the pins will be more reflective of a position or form of the tooth.

An upper opening of the pin holder is filled by a syringe with an impression material or other similar material. Then a rubber base is fitted in over the impression material to fill the pin holder. The combined impression material and rubber base are then removed from the pin holder after the material has set up. The impression analyzer will:

1. take a perfect impression of a prepared tooth every time, and 2. the metal pins will not move once the impression material and rubber base have set up.

A perfect impression will be taken in blood, saliva or along the gum line in this way without being affected by the conditions present in the mouth of a patient.

The impression analyzer is made in different sizes to fit each different sized tooth. The pins will also not come out of the impression material until it is desired. The pin tray is disposable and a new pin holder is used for each tooth of each patient.

Accordingly, it is an object of the present invention to provide a tooth preparation instrument and system of its use including preparing an impression of a portion of a mouth in which a diseased tooth is located and simultaneously preparing or using a pre-formed permanent crown during the same office visit during which the impression was made with the crown having a predetermined internal recess calculated to exactly match a predetermined prepared tooth size so that the crown may be permanently secured to the prepared tooth during a single office visit.

It is another object of the present invention to prepare a tooth based upon a predetermined internal recess of the crown so that the internal recess of the crown will match the prepared tooth for permanently securing the crown during a single office visit.

It is yet another object of the present invention to control the preparation of a tooth for receipt of a crown so that the external dimensions of the prepared tooth coincide with the internal dimensions of the crown and the exterior surface of the crown matches the original shape of the tooth prior to preparation, including taking an impression of the tooth, preparing the crown and installing the crown during a single office visit.

It is still yet another object of the present invention to televise a prepared tooth and compare the televised image against a pre-prepared crown die so that inconsistencies between the two may be noted and corrected.

It is still yet another object of the present invention to televise a prepared crown and by computer software imaging compare the televised image against a pre-prepared crown die by superimposing the two images and rotating the two images through 360° for viewing any inconsistencies relative to the two images and including markings so that a dentist may understand the proper orientation of any corrections to be made.

It is also another object of the present invention to locate a pin holder over a prepared tooth so that a series of constant length, parallel extending pins engage at a lower end the prepared tooth and form at an upper end of the pins a mirror image of the prepared tooth so that after including impression material at the upper end of the series of pins, a molded impression may be compared to a preformed die for a crown so as to note any inconsistencies between the prepared tooth and the die used to form a crown to be inserted on the prepared tooth.

These and other objects of the invention, as well as many of the intended advantages thereof, will become more readily apparent when reference is made to the following description taken in conjunction with the accompanying drawings.

BRIEF DESCRIPTION OF THE DRAWINGS

FIGS. 12-14 illustrates different views of a display monitor that show proper positioning of the disk-burr in FIG. 12, a deviation of the disk-burr in FIG. 13, and a return of the disk-burr to the correct grinding position in FIG. 14.

FIG. 15 is a side view of a convex disk-burr for recessing the flattened occlusal surface of the tooth.

FIG. 16 is a bottom view of the disk-burr shown in FIG. 15.

FIG. 17 is a side view with a convex recessed portion of the tooth shown in dotted lines after application of the disk-burr of FIG. 15.

DETAILED DESCRIPTION OF THE PREFERRED EMBODIMENTS

Figure 1:
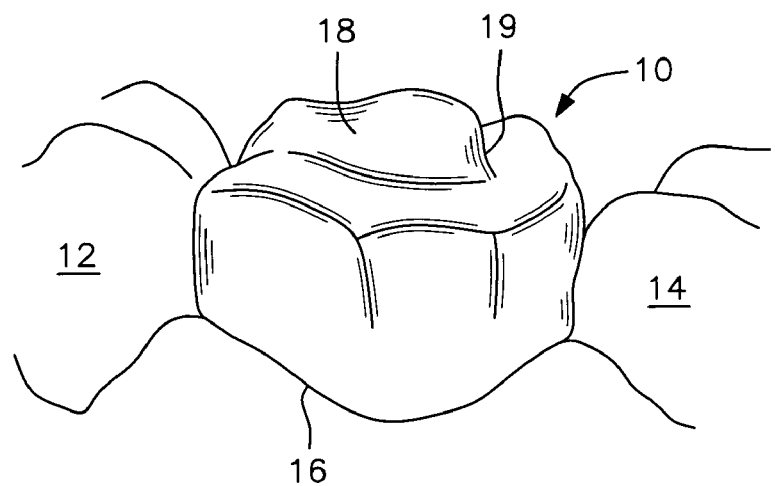
FIG. 1 is a perspective view of a tooth to be treated by the method, apparatus and system of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general and to FIGS. 1 through 5, in particular, the method, apparatus and system embodying the teachings of the subject invention is shown. With reference to FIG. 1, a tooth 10 is shown located between two adjacent teeth 12 and 14, extending below a gum line 16.

Figure 2:
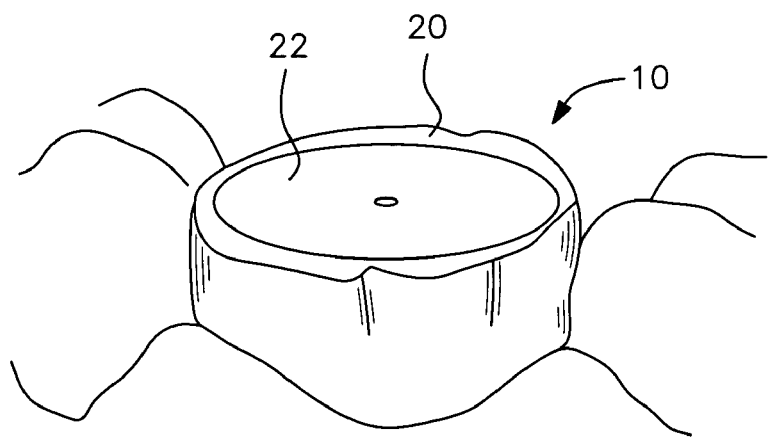
FIG. 2 is a perspective view of a tooth having a flat surface ground on the top of the tooth and a round pattern disk being placed on top of the flat surface.

In FIG. 2, after an impression has been made of the tooth, the tooth 10 has had its upper surface 18 ground into a flat surface 20 which is approximately at a depth of the lowest indentation 19 projecting downwardly from the upper surface 18 in the pretreated tooth 10. The flat surface 20 will provide a reference plane for further treatment of the tooth 10 by attaching a crown to the tooth.

A perfectly round pattern disk 22 of paper, plastic or other disposable material of an appropriate size for each tooth so as to form a complete circle within the confines of all lateral edges of the flat surface 20 of the tooth is selected and placed on top of the flat surface 20 of the tooth 10. A bottom surface of the disk 22 includes an adhesive to maintain the positioning of the disk 22.

Figure 3:
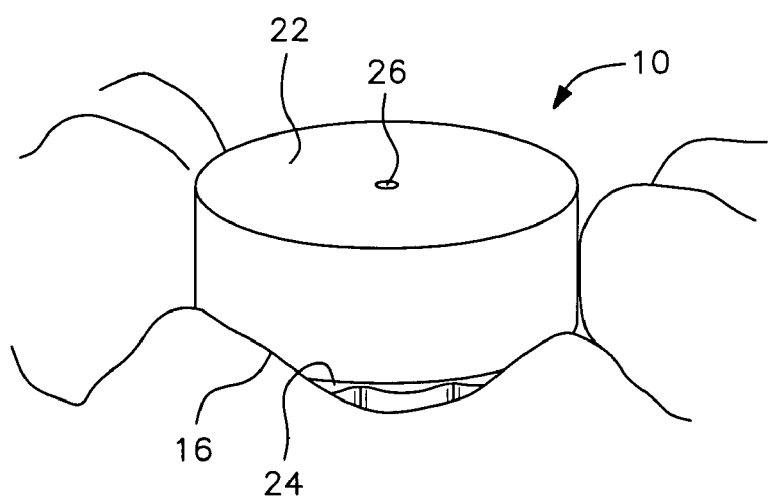
FIG. 3 is a perspective view of a tooth having an upper portion ground into a cylindrical configuration approximating the diameter of the disk placed on top of the tooth as shown in FIG. 2.

The pattern disk 22 is used as a guide to grind the sides of a tooth 10 to a nearly perfect cylindrical shape as shown in FIG. 3. A shoulder 24 of the tooth is maintained at the bottom of the cylindrically shaped portion, adjacent to the gum line 16. At the flat surface 20 of the tooth is drilled a hole 26 of an approximate depth of ⅛ of an inch and having a diameter of approximately 1/32 of an inch.

Figure 4:
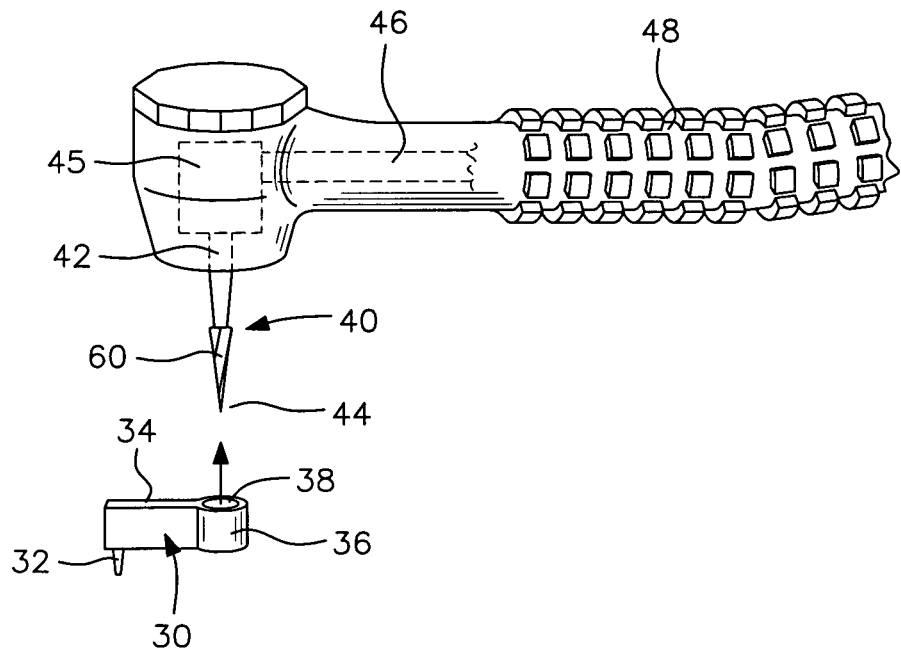
FIG. 4 is an exploded view of a compass grinder and a drill bit located in a hand piece providing a rotating force to the drill bit.

In FIG. 4, a compass grinder guide 30 is shown having a tapered pin 32 at one end of the compass grinder guide for engaging the hole 26 on the top of the tooth. A radially extending bar portion 34 interconnects the pin 32 with an annular drill bit holder 36 having a hollow portion 38 for receipt of a drill bit.

A drill bit 40 has one end 42 mechanically anchored by a snap connection in a drill head 45. The drill head 45 is connected to a drive shaft 46 which extends through a handle portion 48 of a dentist drill. The shaft 46 and drill head 45 impart high speed rotational force to drill bit 40.

The drill head 45 may be air or battery driven. Alternatively the drill head and the shaft are removable from the handle portion 48 so as to limit the portion of the instrument that would need to be sterilized between different patients.

An internal lubrication system may be used to minimize drag on the drive mechanism of the drill bit. An edible oil, such as peanut oil, may be used to lubricate parts of the drill as necessary.

At the opposite end 44 of the drill bit 40 is located a tapered drill portion 46. The angle of taper and length of the drill portion 46 is varied depending upon the inclination and depth desired for the tooth prepared to receive a crown.

Figure 4A:
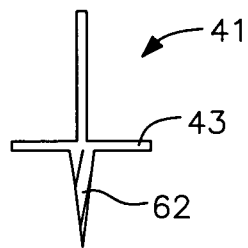
FIG. 4A is an alternate embodiment of a drill bit.

In FIG. 4A, an alternate drill bit 41 is shown. In this drill bit, a radially extending plate 43 located above the drill portion 45 provides a limit or stop to the depth of drilling possible by the drill portion 45. The plate 43 will engage the top of the prepared tooth to prevent further downward drilling.

Figure 4B:
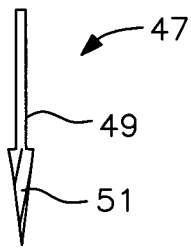
FIG. 4B is another alternate embodiment of a drill bit.

In FIG. 4B, drill bit 47 includes a narrowed diameter shank 49 as compared to larger diameter drill portion 51. The shank 49 visually alerts the dentist to desist from further drilling due to having reached a predetermined depth as measured by the height of drill portion 51.

Figure 5:
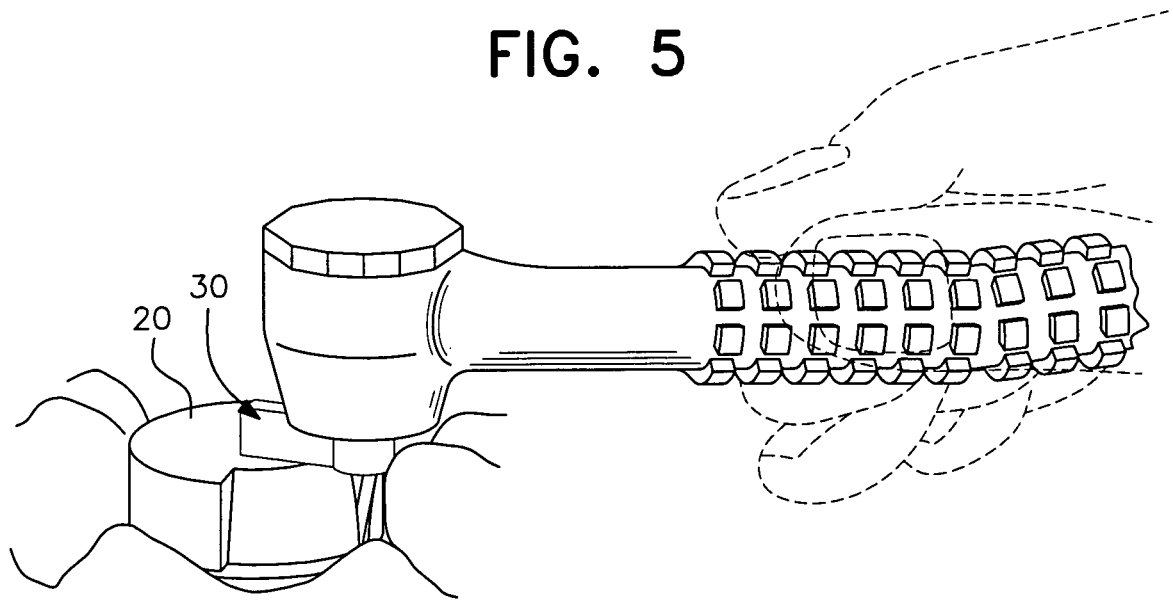
FIG. 5 illustrates the use of the compass grinder of the present invention to impart a predetermined angle of taper to a side wall of a prepared tooth.
Figure 6:
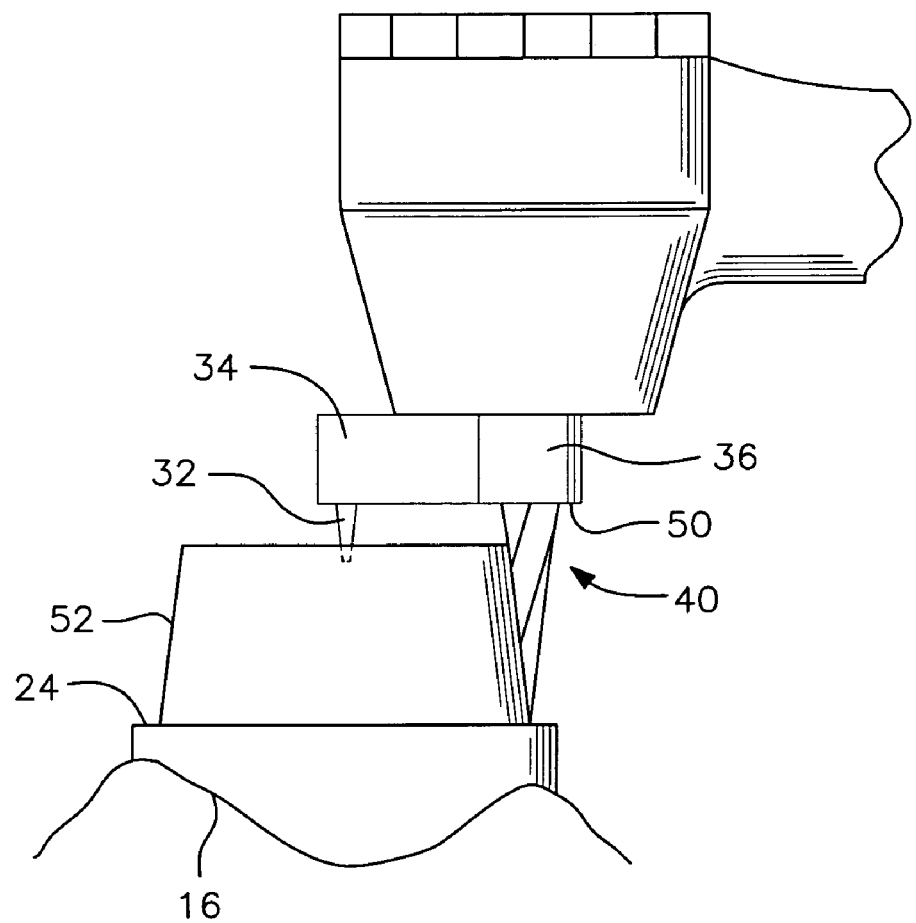
FIG. 6 is a side view illustrating application of a predetermined angle to a predetermined depth into a cylindrically formed upper portion of a tooth.

As shown in FIGS. 5 and 6, the compass grinder guide 30 is anchored in the upper surface 20 of a prepared tooth after removal of the pattern disk 22. The pin 32 engages in the hole 26 of the upper surface of the tooth. The drill bit 40 extends through the hollow portion of the bit holder 36. The drill bit 40 is set into the bit holder 36 to a predetermined depth so that the drill bit 46 will project from below a bottom surface 50 of the bit holder 36 to a predetermined depth.

Figure 7:
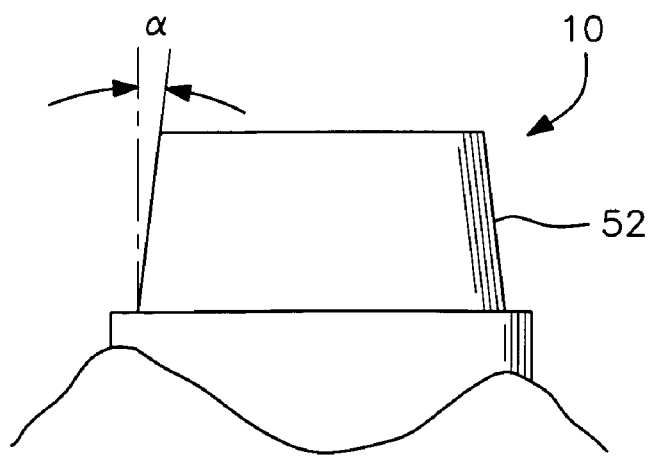
FIG. 7 is a side view illustrating the predetermined angle imparted to an upper portion of a prepared tooth.

By anchoring the pin 32 in the hole 26 and rotating the drill handle about the hole 26, using the hole 26 as a central axis, the grinding away of the tooth, as shown in FIG. 5, produces a truncated cone portion 52 as shown in FIGS. 6 and 7. Depending upon the angle of taper of the drill bit 46, the angle α, preferably between 1 and 10°, and more preferably between 3 and 8°, as shown in FIG. 7, will be varied to impart a predetermined taper to the upper portion of the tooth being prepared to receive a crown.

Simultaneously with and in preparation of securing a crown to a tooth, a crown is prepared by a lab technician having an internal recess of a predetermined base diameter, a predetermined depth and a predetermined diameter at the uppermost portion of the recess of the crown. The internal recess of the crown will exactly fit on the truncated conical portion 52 of the tooth 10 simultaneously prepared by the dentist, as shown in FIG. 7.

Figure 8:
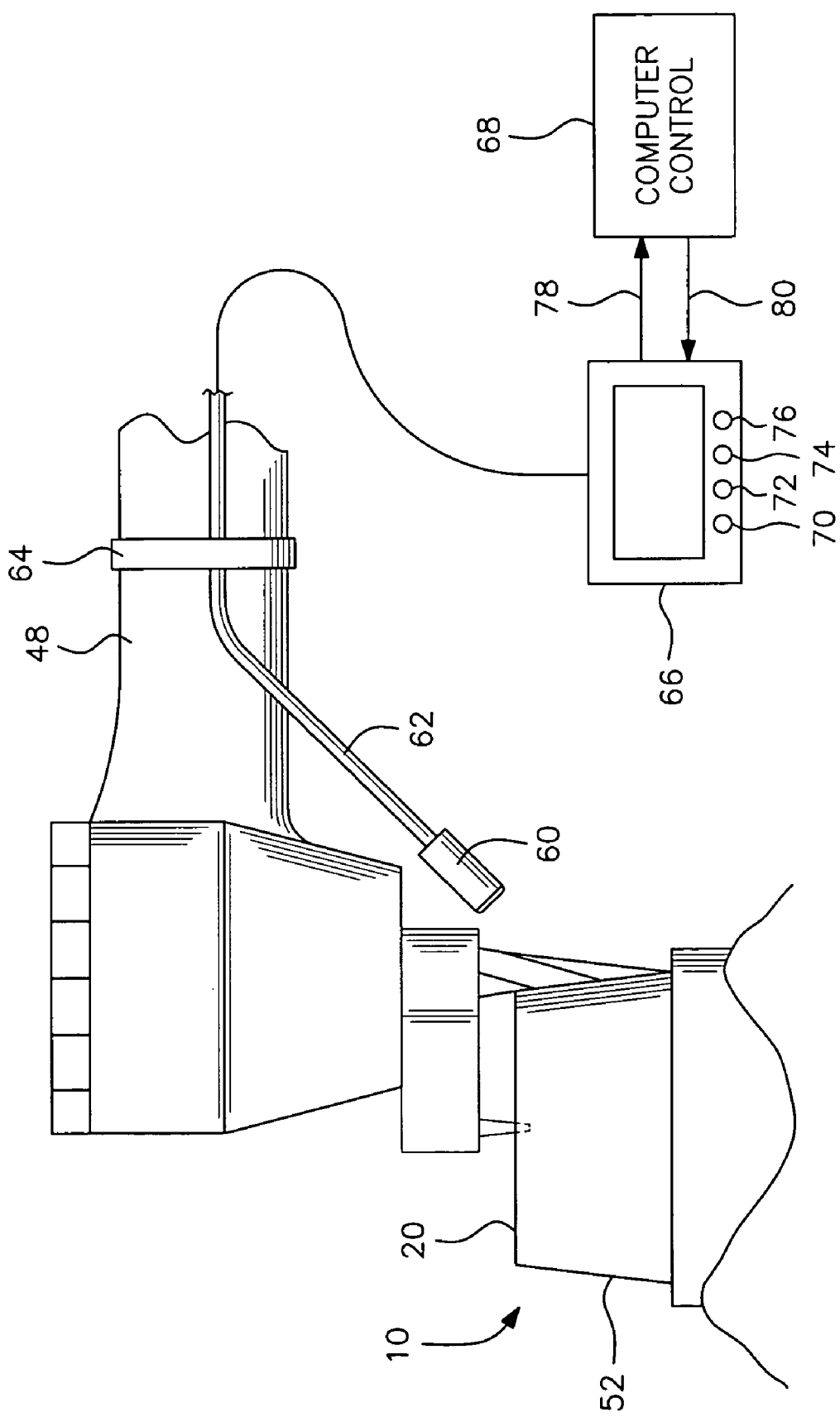
FIG. 8 illustrates the process of monitoring the drilling process and alerting a dentist to the correctness of the desired depth and angle of removal of tooth material.

As shown in FIG. 8, the grinding of the tooth 10 may be monitored by a television camera 60 having an optic fiber cable 62 secured to the handle 48 of the drill by a band 64. The cable transmits an image of the grinding operation to a monitor 66 and a computer controller 68 by line 78. The computer controller 68 activates a series of four lights 70, 72, 74 and 76 by line 80 depending upon the accuracy of the procedure being performed.

For example, a green light 70 would be activated to indicate that the compass grinder is positioned parallel to the upper surface 20 of the tooth. A blue light 72 would indicate that a desired depth or inclination is being achieved by the drill bit as also limited by the length of the burr. Alternatively, different sized burrs can be used to change the depth of penetration into the tooth. A red light 74 would warn that the drill bit is tilted creating an undercut whereas a yellow light 76 would indicate that an outward tilting of the drill bit is occurring to create an increased diameter portion of the truncated conical portion 52 or that the desired cutting depth is close to being achieved.

These lights as controlled by controller 68 will ensure an accurate mating of the prepared tooth with the simultaneously prepared crown which is made on the basis of an impression of the original tooth configuration as shown in FIG. 1. Based upon the knowledge that the upper surface of the prepared tooth will be flat at the deepest groove of its original surface and that a predetermined drill bit will be used to introduce a predetermined angular inclination of a tapered conical portion, to a predetermined depth, a crown can be prepared so that the crown may be secured to the tooth at the time of preparation of the tooth without a need for a subsequent office visit by the patient.

Figure 9:
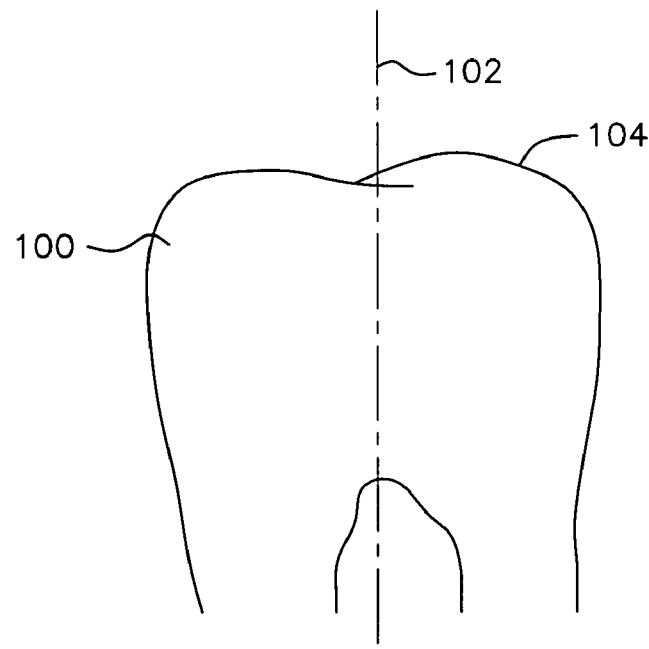
FIG. 9 illustrates a typical tooth to which the present invention is applied and including its central longitudinal axis.
Figure 10:
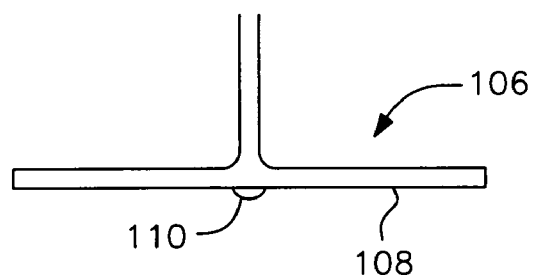
FIG. 10 is a side view of the disk-burr used to prepare the occlusal surface of a tooth.
Figure 11:
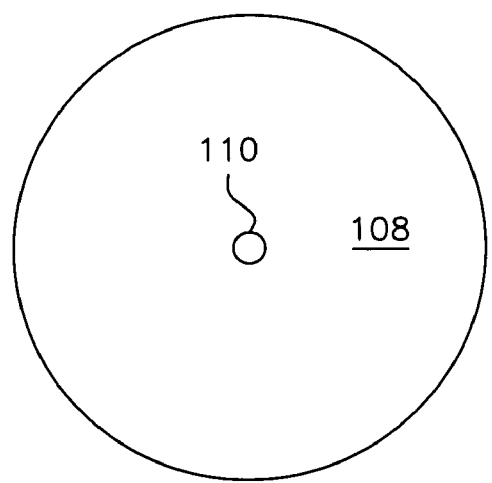
FIG. 11 is a bottom view of the disk-burr of FIG. 10.
Figure 18:
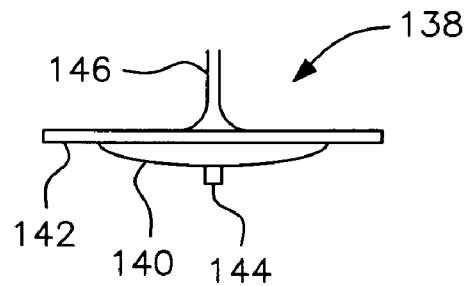
FIG. 18 is a side view of a disk-post which matches the depression created by the disk-burr of FIG. 15.
Figure 19:
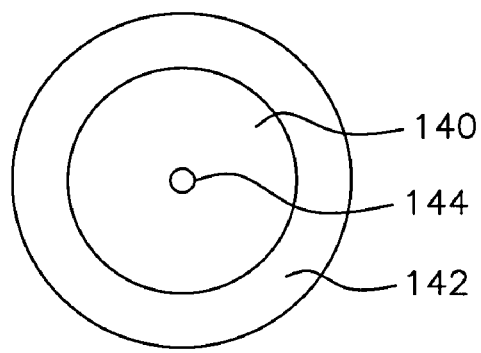
FIG. 19 is a bottom view of the disk-post shown in FIG. 18.
Figure 20:
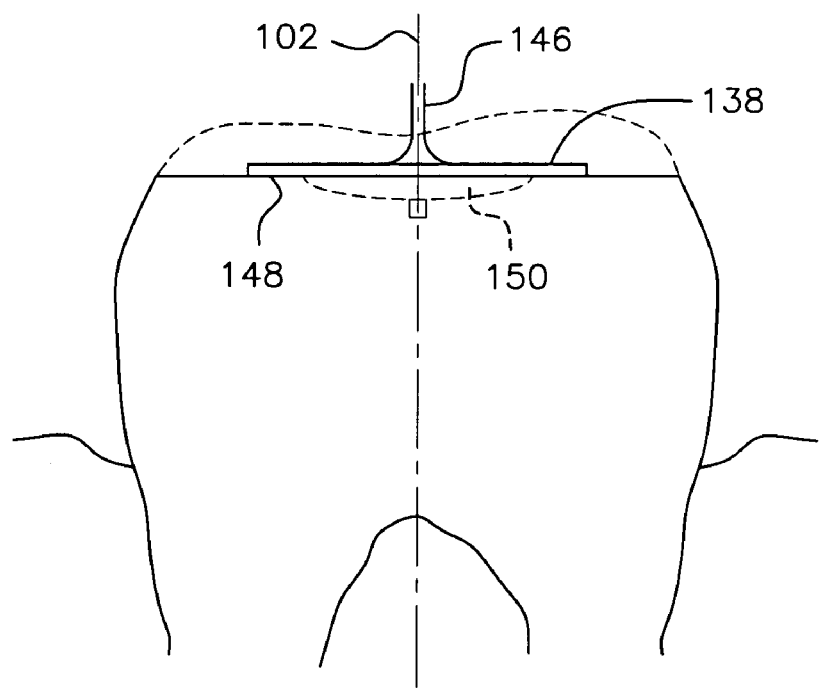
FIG. 20 schematically illustrates the disk-post of FIG. 18 secured to the occlusal surface of a tooth with a bonding agent.

In FIG. 9, a tooth 100 is shown to which an alternate form of the present invention is to be applied with reference to its central longitudinal axis 102. Initially, the occlusal surface of the tooth 104 is flattened by a disk-burr 106 having a lower flat grinding surface 108 and a centrally located projection 110 to provide a depressed anchoring surface for a convex disk-burr.

During grinding of the tooth 100, the dentist may refer to a display monitor having schematic illustrations similar to those shown in FIGS. 12 through 14. The monitor images 112, 114 and 116 show three various drilling positions of the disk-burr 106.

In FIG. 12, a steady light 118 in the center of the display 112, indicates a correct orientation of the disk-burr 106 as the upper surface of the tooth is removed. If the position or inclination of the disk-burr relative to the central longitudinal axis 102 of the tooth 100 should drift, a blinking light 120 positioned towards a peripheral edge of the display 114, as shown in FIG. 13, would tend to indicate to the dentist that a correction needs to be made to return to a central grinding of the tooth. An arrow 122 indicates to the dentist the direction of drift of the disk-burr 106.

During correction of the grinding, an arrow 124 in the display 116 indicates to the dentist that movement is being made in the correct direction. Correction is continued until a steady central light 118 will confirm correct grinding positioning.

To prepare the flattened surface 126 of the tooth for creating a shoulder at the gum line of the tooth, a convex disk-burr 128 is used having a convex grinding surface 130 projecting from the bottom surface 132 and terminating in a projection 134. Projection 134 is placed in the corresponding recess formed by the projection 110 from disk-burr 106. As shown in FIG. 17, a recess 136 corresponding to the shape of the disk-burr is made in the surface 126. A disk-post 138, corresponding in dimension to the disk-burr 128 is selected having a complementary shaped convex portion 140 projecting from a lower surface 142 and terminating in a projection 144 which will fit in a corresponding recess drilled by the disk-burr 128.

On the opposite side from bottom surface 142 is centrally located post 146. The disk-post 138 is cemented by a bonding agent 148 in the recess 150 formed by the disk-burr 128 so that the post 146 extends along the longitudinal axis 102 of the tooth.

Figure 21:
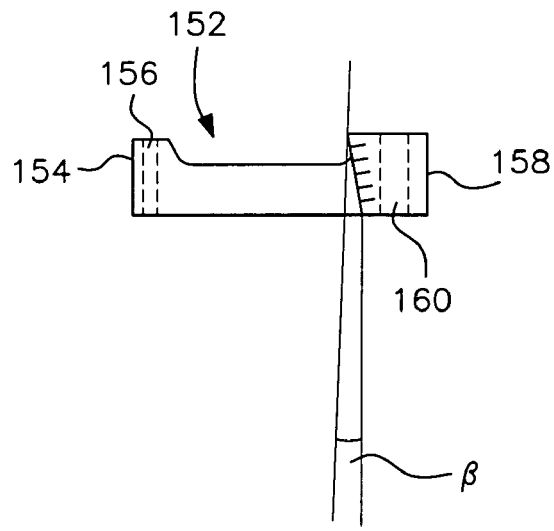
FIG. 21 illustrates a radial arm for securing onto the centrally extending post of the disk-post and having an opposite end for holding a removable burr.
Figure 22:
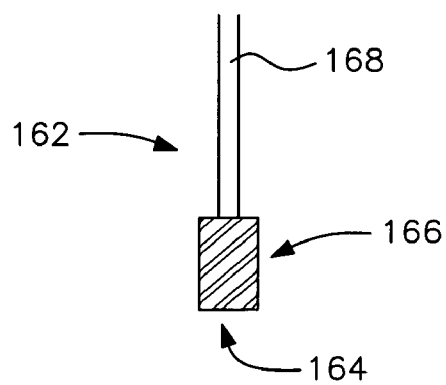
FIG. 22 is a side view of the removable burr intended to cooperate with one end of the radial arm shown in FIG. 21.

Associated with each particular disk-post 138 is a radial arm 152, as shown in FIG. 21. At one end 154, a hole 156 is provided which matches the diameter of the post 146 on the disk-post 138. At the opposite end 158 is an opening 160 which is positioned at an angle to the disk-post 146, with the angle β ranging from 5 to 7 degrees. A removal burr 162 having a slightly convex abrasive surface 164 at its bottom and an abrasive milling surface 166 at its sides, is placed by its shaft 168 in opening 160 of the radial arm 162.

Figure 24:
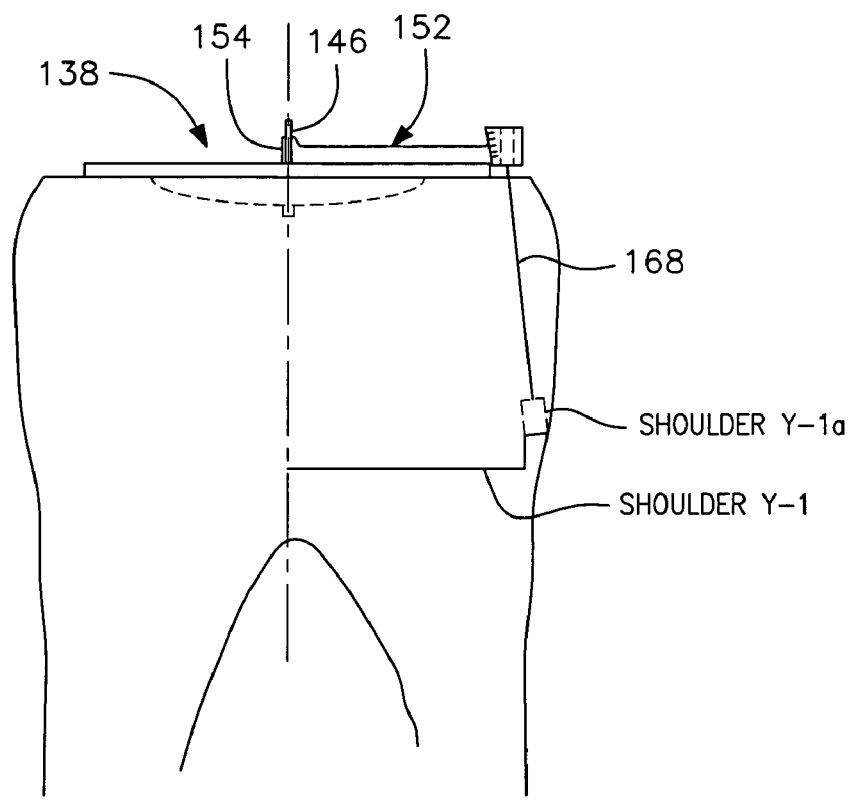
FIG. 24 schematically illustrates the assembly of the present invention and including a radial arm pivotally mounted on a disk-post and including a removable burr for creating a shoulder on the tooth at the gum line.
Figure 25:
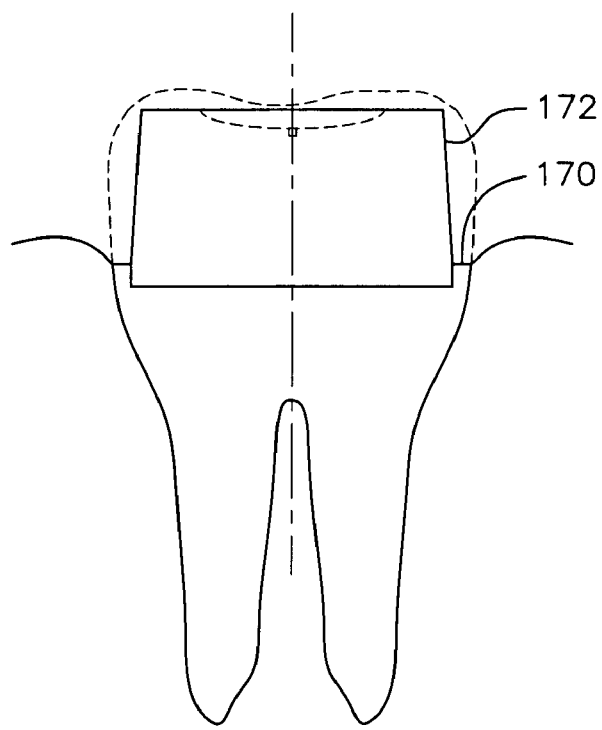
FIG. 25 schematically illustrates the prepared tooth awaiting receipt of a crown, the dotted lines being illustrative of the ground away portion of the tooth.

As shown in FIG. 24, the removal burr is rotated about the side of the tooth with end 154 of radial arm 152 pivotally rotated about post 146 secured in the upper surface of the tooth. The dentist stops removal of material when the removal burr has reached the shoulder level Y-1a. Additional material is removed in 1 mm increments down to a lower shoulder level Y-1 based upon the desired depth of the shoulder 170 to be formed. The side wall 172 of the tooth is formed at an angle depending upon the angle of inclination of the removal burr in the radial arm.

Figure 23:
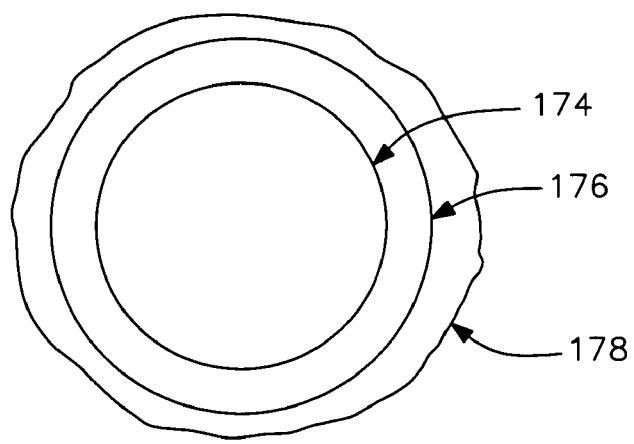
FIG. 23 is a plan view illustrating the various tiers provided by a prepared tooth, a shoulder of the prepared tooth and the outer perimeter of the tooth at the gum line.

As shown in FIG. 23, the tooth includes an outer perimeter 174 at the top of a prepared tooth, an outer perimeter 176 at the base of the prepared tooth and an outer perimeter 178 at the shoulder gum line. Corresponding measurements for an individual tooth are separately being used to prepare a crown which will be perfectly aligned with the tooth having material removed according to the method of the present invention using the described tools.

With reference to the drawings, in general, and to FIGS. 26 through 30, in particular, a dental computer analyzer embodying the teachings of the subject invention is generally designated as 200.

Figure 26:
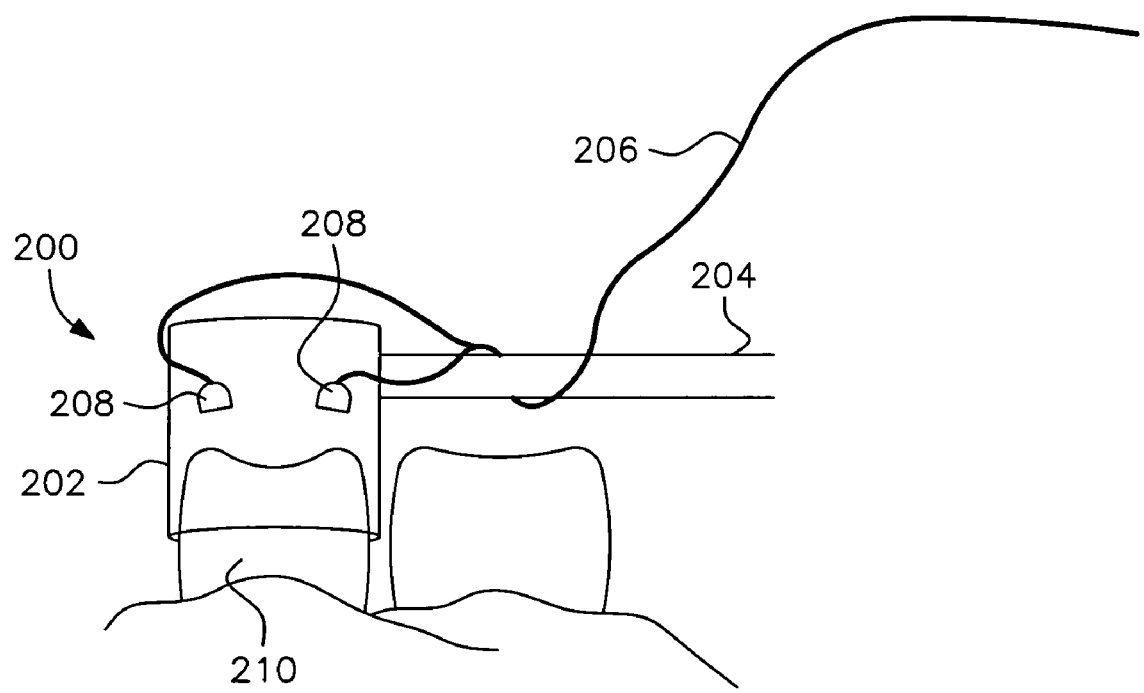
FIG. 26 is a schematic illustration of a dental computer analyzer fit over a tooth in its intact form so that a computer digital image may be taken of the appearance of the tooth prior to its preparation.

With reference to its orientation in FIG. 26, the dental computer analyzer includes a housing 202 supported by a manipulable arm 204. The housing 202 is connected to a CPU interface cable 206. The cable 206 is connected to at least one television or video camera 208 which is located inside the housing 202.

In FIG. 26, the housing 202 is fit over a tooth 210. Various images are taken of the tooth for later comparison and production of a crown matching in contour in color to the original tooth. The information about the tooth is transmitted in digital form by the CPU interface cable for storage, retrieval and comparison with other digital information.

Figure 27:
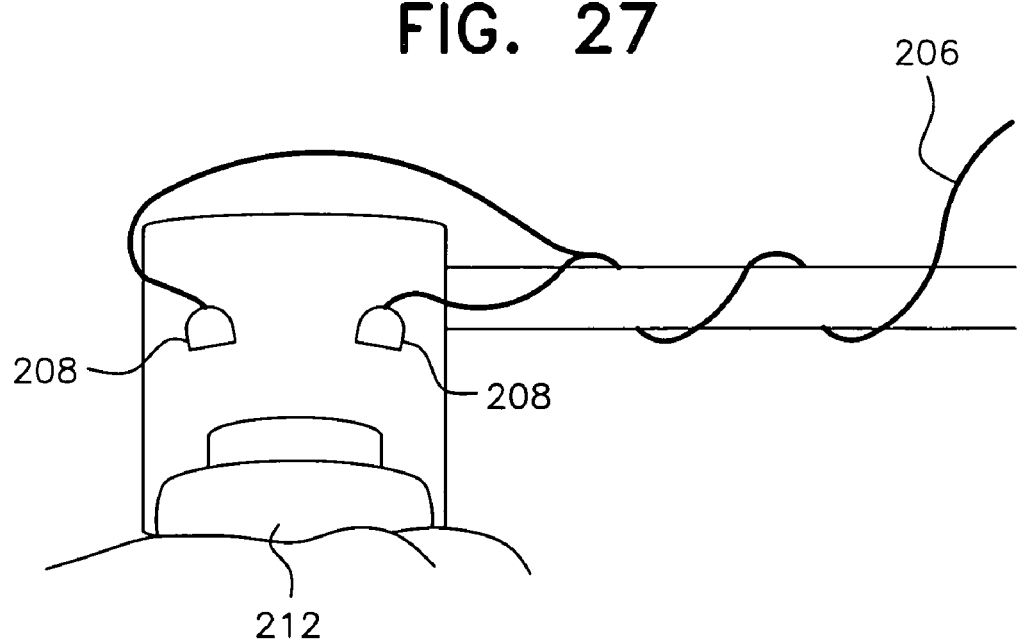
FIG. 27 schematically illustrates the dental computer analyzer televising an image of a prepared tooth for a comparison with a prepared die image which was used to prepare a crown.

As shown in FIG. 27, a prepared tooth 212 is digitally captured by the at least one camera 208 for comparison with a pre-prepared crown die. The crown die is used for forming a crown to be fitted over the prepared tooth 212.

Figure 28:
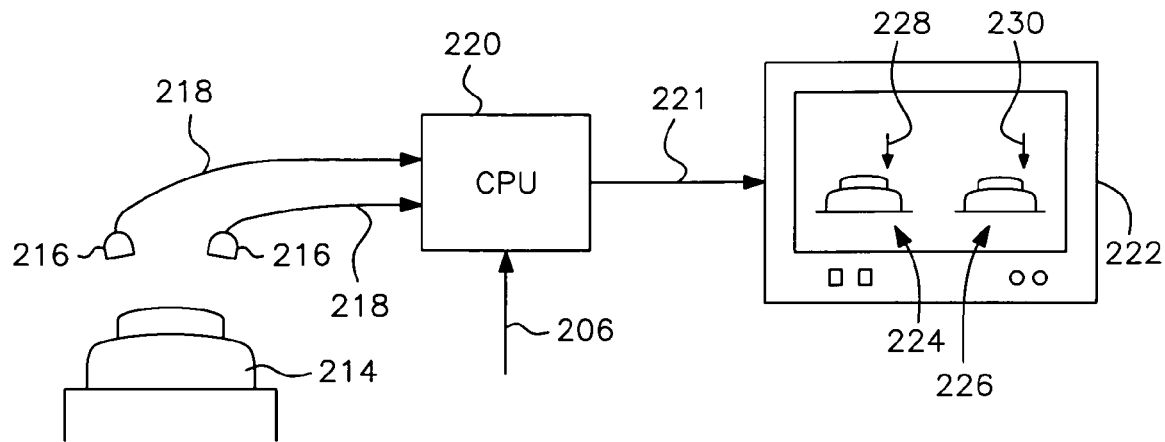
FIG. 28 schematically illustrates the capturing of a digital image of a prepared die for transmission to a digital processor and comparison of an image of a actual prepared tooth for viewing on a television monitor.
Figure 29:
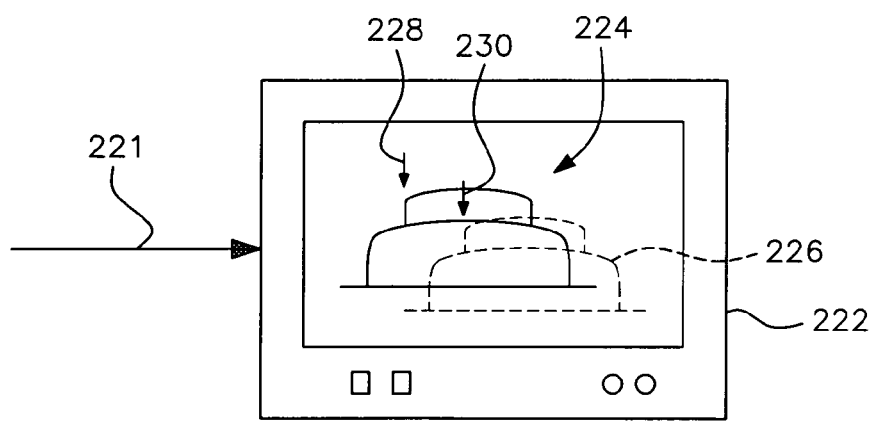
FIG. 29 schematically illustrates the overlaying of the image of a prepared tooth and image of a crown die with appropriate notation of relative position points.
Figure 30:
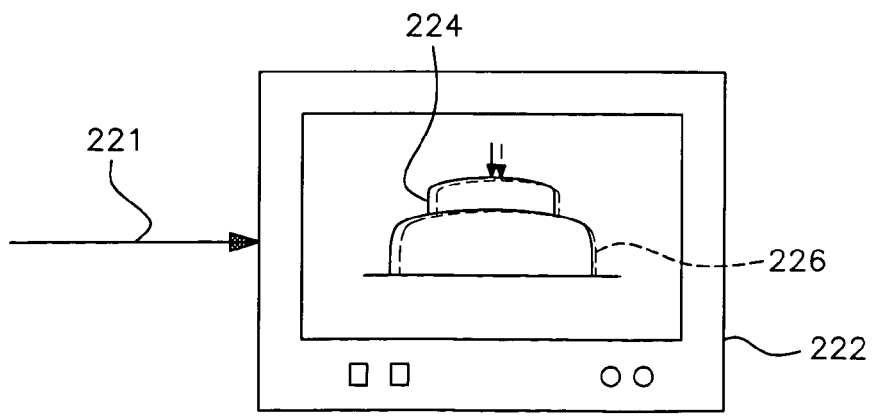
FIG. 30 schematically illustrates an almost complete overlap of the images of a prepared tooth and a crown die for visualization of any inconsistencies.
Figure 31:
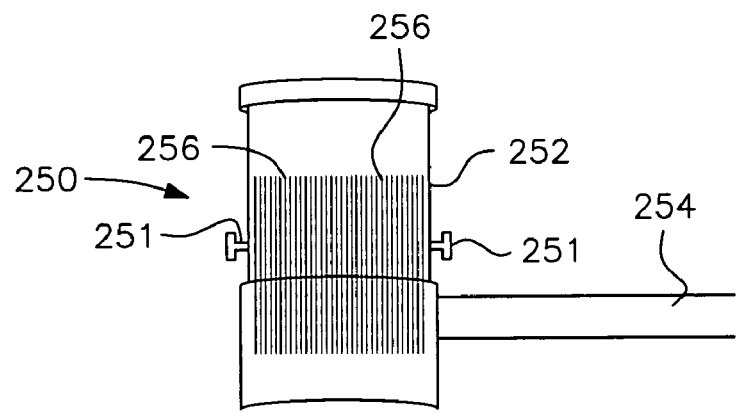
FIG. 31 schematically illustrates a pin holder of an impression analyzer to be placed over a tooth for recreating the contours of an original tooth and a prepared tooth.
Figure 32:
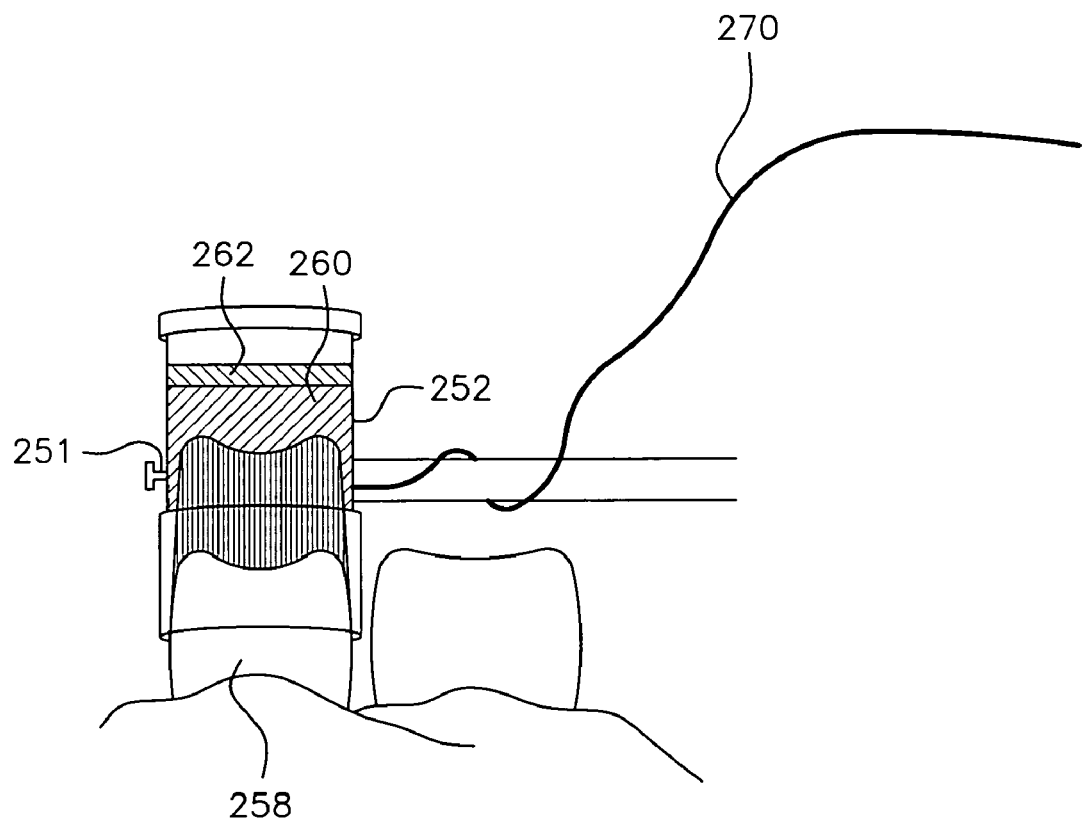
FIG. 32 schematically illustrates the application of the impression analyzer onto an existing tooth to capture the contours of the tooth prior to removal of tooth material.

As shown in FIGS. 28 through 30, a crown die 214 is digitally captured by at least one camera 216 and transmitted by CPU interface cable 218 to a central processing unit (CPU) 220. The die 214 may be located at a remote location and an image electronically transmitted to the CPU 220.

The captured image of the prepared tooth is similarly transmitted to CPU 220 by CPU interface cable 206. Software in the CPU 220 produces signals transmitted over image transmission cable 221 to allow a side-by-side comparison on a monitor 222 of an image 224 of the prepared tooth 212 and an image 226 of the crown die 214.

Incorporated into the displayed images is an identifying arrow or indicia 228, 230, respectively, to identify the same position or view of both the images 224, 226 so as to identify disparities between the images. It is also possible by manipulation of the software of the CPU to overlay the images 224, 226 relative to each other as shown in FIG. 29, while simultaneously using the identifying arrow or indicia 228, 230, respectively, for a closer comparison of the images.

It is possible to match the position of the two images 224, 226 with a slight offset as shown in FIG. 30 or to position the images directly on top of one another for immediate identification of discrepancies between the images of the prepared tooth and the crown die. It is also possible for the dentist to view the superimposed images on the monitor 222 for immediate correction of the prepared tooth for receipt of a crown which would perfectly fit on both the crown die and the prepared tooth. Adjustments to the prepared tooth are immediately viewable on the monitor 222. A videotape of this process may be recorded for subsequent viewing by the patient.

By the use of the computer analyzer of the invention, crown preparation may be performed by running a probe over an exterior surface of the tooth to be replaced. Signals generated by the probe may be relayed to a remote location for coordinated movement of a grinding drill bit to create an exact duplicate on the prepared crown of the original configuration of the to be replaced tooth. This process, when complete, will produce a crown identical to the original tooth.

In another embodiment of the present invention as shown in FIGS. 31 through 34, a dental impression analyzer 250 includes a housing 252 secured to a handle 254. Optionally, a data interface cable 270 may be connected to the housing 252 for internal viewing of the housing for purposes similar to the dental computer analyzer as previously discussed.

In a portion of the housing tube 252 are located a plurality of identical length and diameter, stainless steel or plastic pins 256 which are tightly compressed together in the interior of the housing 252. While extending parallel and in contact with each other, the pins are slidably movable in the housing 252 upon encountering an object. The pins include a low friction coating to enable the sliding of one pin relative to the others.

Therefore, when the housing 252 is placed in contact with a tooth 258, with the lower ends of the pins 256 engaging the various contours of the tooth 258, the upper opposite ends of the pins assume a contour identical to the contour of the tooth engaged by the lower end of the pins. By the vertical shifting of the pins, an exact replica of the configuration of the tooth can be formed. This form can be used to produce a crown which would be identical in contour to that of the original tooth.

To lock the position of the upper end of the pins in place, at least one set screw 251, extending through a side wall of the housing is tightened to lock the position of the pins 256. An impression material 260 is placed over the top of the pins 256. Then a rubber base 262 is applied to further seal the position of the impression material and to further lock the position of the upper ends of the pins in place.

The impression analyzer 250 is then removed from the tooth for positioning of the housing 252 onto a crown so that the lower ends of the pins contact the crown to see if the contours are identical with that of the original tooth.

Figure 33:
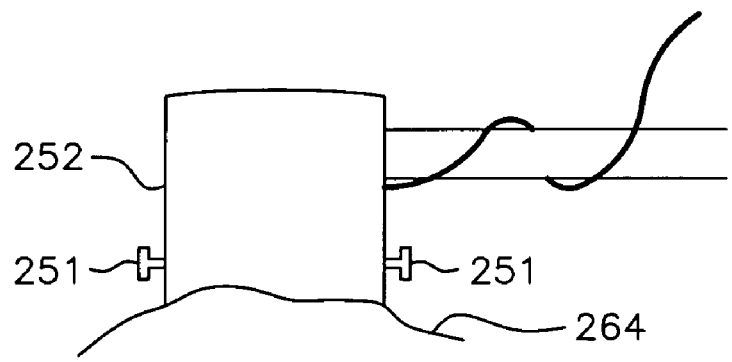
FIG. 33 illustrates the placement of the impression analyzer over a prepared tooth.
Figure 34:
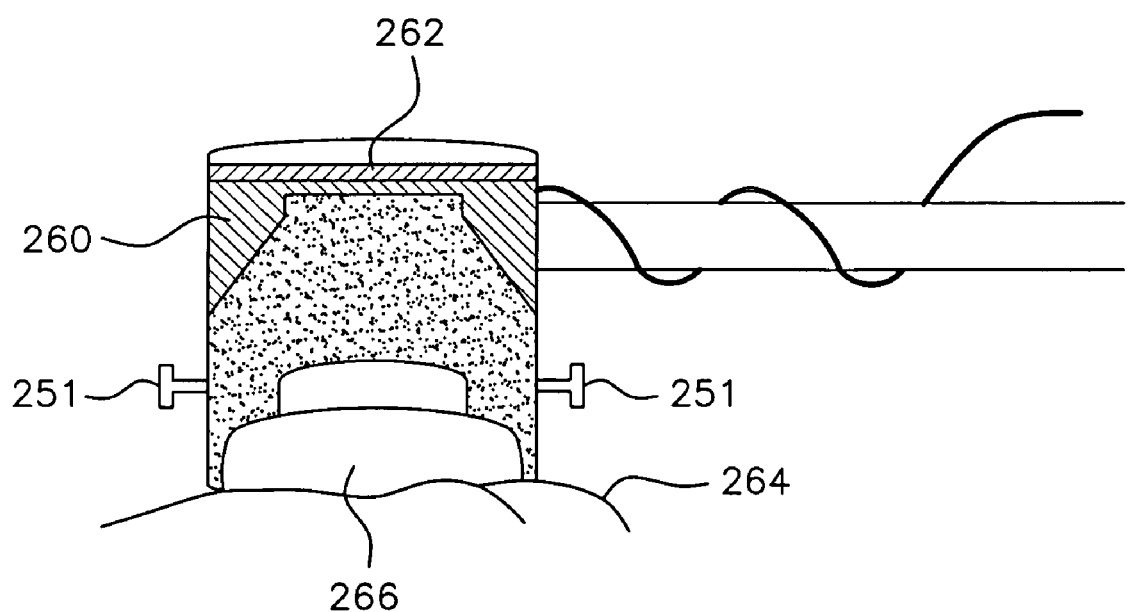
FIG. 34 is a sectional view of FIG. 33 illustrating the assumption of the location of the pins approximating the contour of the prepared tooth with impression material and a rubber base securing the upper ends of the pins in place.

Similarly, as shown in FIG. 33, the housing 252 is placed down to the gum line 264 of the mouth of the patient. The housing would thereby surround a prepared tooth 266 and have the pins 256 contact the upper surface of the prepared tooth. The upper end of the pins would thereby be positioned into the same shape as the upper surface of the prepared tooth 266. As in FIG. 32, impression material 260 and rubber base 262 fill the housing to lock the position of the upper end of the pins. The housing is then removed from the prepared tooth and the locked position of the lower end of the pins can be used to help create a crown die to be used for formation of a socket of a crown to perfectly fit on top of the prepared tooth.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A dental impression analyzer comprising:
a housing having two opposite open ends,
a lower end of the two opposite ends fitting over a tooth of a patient,
a plurality of pins slidably mounted in the housing, said pins being of equal length, extending parallel to each other, and at least a portion of sidewalls of the housing extending parallel to each other and parallel to the plurality of pins to maintain the pins parallel to each other and to guide movement of the pins, said plurality of pins being tightly compressed together in an interior of the housing, a lower end of the pins being positioned to engage an uppermost surface of the tooth of the patient when the housing is fitted over the tooth of the patient, and an upper end of the pins replicating the uppermost surface of the tooth when the lower end of the pins engage the uppermost surface of the tooth.

2. The dental impression analyzer as claimed in claim 1, wherein a handle is connected to said housing.

3. The dental impression analyzer as claimed in claim 1, wherein said pins are made of stainless steel.

4. The dental impression analyzer as claimed in claim 3, wherein said pins are coated with a low friction lubricant.

5. The dental impression analyzer as claimed in claim 1, wherein an impression material is located in said housing at an upper end of the two opposite ends of the housing for holding a position of the upper ends of the pins.

6. The dental impression analyzer as claimed in claim 5, wherein a rubber base is placed on top of the impression material to secure the impression material in place.

* * * * *